US008535468B2

(12) United States Patent
Konthieng et al.

(10) Patent No.: US 8,535,468 B2
(45) Date of Patent: Sep. 17, 2013

(54) METHOD FOR MAKING DISPOSABLE BODILY FLUID HANDLING COMPOSITE PAD

(75) Inventors: Ranida Konthieng, Chachoengsao (TH); Hidenori Sato, Kagawa (JP); Makoto Suekane, Kagawa (JP)

(73) Assignee: Uni-Charm Corporation, Shikokuchuo-Shi, Ehime (JP)

( * ) Notice: Subject to any disclaimer, the term of this patent is extended or adjusted under 35 U.S.C. 154(b) by 733 days.

(21) Appl. No.: 12/524,055

(22) PCT Filed: Jul. 21, 2009

(86) PCT No.: PCT/JP2009/063020
§ 371 (c)(1),
(2), (4) Date: Oct. 2, 2009

(87) PCT Pub. No.: WO2011/001542
PCT Pub. Date: Jan. 6, 2011

(65) Prior Publication Data
US 2011/0155298 A1    Jun. 30, 2011

(30) Foreign Application Priority Data

Jun. 30, 2009  (JP) ................................. 2009-156294

(51) Int. Cl.
*B29C 59/04*  (2006.01)
*A61F 13/47*  (2006.01)

(52) U.S. Cl.
USPC ........................... 156/209; 156/199; 604/389

(58) Field of Classification Search
None
See application file for complete search history.

(56) References Cited

U.S. PATENT DOCUMENTS

| 4,862,574 | A | 9/1989 | Seidy |
| 5,910,137 | A * | 6/1999 | Clark et al. .................... 604/387 |
| 6,171,425 | B1 | 1/2001 | Nukina et al. |
| 2003/0087056 | A1 | 5/2003 | Ducker et al. |
| 2006/0247590 | A1 | 11/2006 | Ito et al. |

FOREIGN PATENT DOCUMENTS

| JP | 1992-35420 U | 3/1992 |
| JP | 10-286280 A | 10/1998 |
| JP | 2001-145659 A | 5/2001 |
| JP | 2004-033348 A | 2/2004 |
| JP | 2006-305243 A | 11/2006 |
| JP | 2007-260875 A | 10/2007 |
| JP | 2008-079827 A | 4/2008 |
| WO | 97/27032 A1 | 7/1997 |

OTHER PUBLICATIONS

PCT/JP2009/063020 International Search Report.

* cited by examiner

*Primary Examiner* — Barbara J. Musser
(74) *Attorney, Agent, or Firm* — Lowe Hauptman & Ham, LLP (57) ABSTRACT

A method and an apparatus are provided for making a disposable bodily fluid handling composite pad having thickness-reduced regions on longitudinally opposite ends. The disposable bodily fluid absorbing composite pad includes a bodily fluid absorbing first pad and a bodily fluid absorbing second pad seperably attached to the first pad. A continuous web having continuous bodily fluid absorbing layer and bodily fluid impervious layer permanently attached together is fed to pass through paired compression rolls to obtain a worked web formed in regions which will become ends of the first pad with thickness-reduced regions. A bodily fluid absorbing web is seperably attached to the worked web to obtain a first composite web. A bodily fluid impervious web, pressure-sensitive adhesive and a separator are placed on the bodily fluid absorbing web of the first composite web to obtain a second composite web from which the composite pad is cut out.

12 Claims, 6 Drawing Sheets

METHOD FOR MAKING DISPOSABLE BODILY FLUID HANDLING COMPOSITE PAD

RELATED APPLICATIONS

The present application is based on, and claims priority from, International Application PCT/JP2009/63020, filed Jul. 21, 2009 and Japanese Application Number 2009-156294, filed Jun. 30, 2009, the disclosures of which are hereby incorporated by reference herein in their entirety.

TECHNICAL FIELD

The present invention relates to method and apparatus for making a disposable bodily fluid handling composite pad adapted to be used, for example, in a form of panty liner or menstruation napkin.

RELATED ART

Composite pads comprising two or more bodily fluid absorbing pads such as panty liners are well known.

For example, a menstruation laminated napkin disclosed in PATENT DOCUMENT 1, Japanese patent Application Laid-Open Publication No. 1998-286280 (JP 10-286280 A), comprises two or more menstruation napkins put flat together seperably attached along peripheral edges of these napkins and the respective napkins are formed at ends thereof with tabs displaced from those of the other component napkin(s). The soiled menstruation napkin can be peeled off from the remaining menstruation laminated napkin by nipping the tabs with fingers.

PATENT DOCUMENT 2, Japanese Patent Application Laid-Open Publication No. 2006-305243 (JP 2006-305243 A), discloses an absorbent article comprises a pair of absorbent components put flat together and separably attached to each other by locally heating them under a pressure. The upper component has its opposite ends compressed to form thickness-reduced regions so that gaps are formed between these thickness-reduced regions and the lower absorbent component underlying the gaps. When the upper component has been soiled, the upper component can be peeled off from the lower component by nipping the ends with the fingers.

CITED REFERENCES

Patent Document

PATENT DOCUMENT 1: Japanese patent Application Laid-Open Publication No. JP 10-286280 A
PATENT DOCUMENT 2: Japanese patent Application Laid-Open Publication No. JP 2006-305243 A

SUMMARY OF THE INVENTION

Problem to be Solved by the Invention

In the case of the laminated menstruation napkin disclosed in PATENT DOCUMENT 1, the respective component menstruation napkins have nipping tabs formed at positions different depending on the respective component napkins. In consequence, the respective component napkins have outlines different one from another. An apparatus to make such respective component napkins into the laminated menstruation napkin should include production lines adapted for the respective component menstruation napkins having different outlines and, therefore, the apparatus should be large in size. Additionally, in such laminated menstruation napkin, if the nipping tabs partially overlap one another, it might be difficult to nip the tab properly.

In the case of the absorbent article disclosed in PATENT DOCUMENT 2, two components having the same contour shape are put flat together and only one of the components is formed with the thickness-reduced ends. One of the components may be easily peeled off from the other component by nipping the thickness-reduced ends. However, this document discloses neither method nor apparatus adapted to form such thickness-reduced ends in an efficient manner and to make the composite absorbent article comprising the components laminated with each other in an efficient manner.

In view of the problem as has been described above, it is a principal object of the present invention to provide improved method and apparatus for a disposable bodily fluid handling composite pad adapted to be used, for example, as a panty liner or a menstruation napkin.

Measure to Solve the Problem

The invention to achieve the object set forth above has a first aspect relating to a method for making the disposable bodily fluid handling composite pad and a second aspect relating to an apparatus for making this disposable bodily fluid handling composite pad.

The object set forth above is achieved, according to the present invention on the first aspect thereof, by an improvement in the method for making a disposable bodily fluid handling composite pad having a longitudinal direction, a transverse direction and a thickness direction being orthogonal one to another, and comprising a bodily fluid absorbing first pad and a bodily fluid absorbing second pad, the first pad comprising a bodily fluid absorbing layer and a bodily fluid impervious layer put flat together in the thickness direction and attached permanently joined together, at least one of opposite ends as viewed in the longitudinal direction is formed so as to be thinner than an intermediate region defined between the opposite ends, and the second pad being separably attached to the bodily fluid impervious layer of the first pad.

The improvement according to the present invention on the first aspect thereof is characterized by comprising steps as follow: feeding a continuous web comprising the bodily fluid absorbing layer and the bodily fluid impervious layer permanently attached to each other in a machine direction, allowing the continuous web to pass between paired compression rolls rotating in the machine direction; compressing a region of the continuous web corresponding to the at least one of the opposite ends by the paired compression rolls to reduce the thickness thereof to obtain a worked web along which thickness-reduced regions are arranged at desired intervals in the machine direction; putting flat and separably attaching a bodily fluid absorbing web to the bodily fluid impervious layer together while feeding any one of the worked web and a plurality of the first pads cut out from the worked web in the machine direction and thereby first composite web is obtained; permanently attaching bodily fluid impervious web to the bodily fluid absorbing web constituting the first composite web; coating the bodily fluid impervious web with pressure-sensitive adhesive by means of which the second pad is separably attached to a garment of a person wearing the composite pad; masking the pressure-sensitive adhesive with a web as stock material for separators to obtain second composite web; and cutting out the composite pad from the second composite web.

According to one preferred embodiment of the invention on the first aspect thereof, the worked web is formed with two or more queues of the thickness-reduced regions arranged in a width direction corresponding to a cross direction orthogonal to the machine direction and a plurality of the first pads can be cut out from the worked web in the width direction.

According to another preferred embodiment of the invention on the first aspect thereof, the step of separably attaching the bodily fluid absorbing web to the bodily fluid impervious layer comprises sub-steps of locally compressing one of the worked web and the first pad together with the bodily fluid absorbing web placed one upon another to form queues of compressed spots at which one of the worked web and the first pad is brought into mechanical entanglements with the bodily fluid absorbing web so that the queues of the compressed spots may partially overlap the thickness-reduced region.

According to still another preferred embodiment of the invention on the first aspect thereof, in each pair of the adjacent queues of the thickness-reduced regions arranged in the width direction of the continuous web, the individuals of the thickness-reduced regions are offset so as not to be adjacent one another as viewed in the width direction of the continuous web.

According to yet another preferred embodiment of the invention on the first aspect thereof, the thickness-reduced region is contoured, on the surface of the bodily fluid absorbing layer, by a pair of side edges extending in parallel to each other in the longitudinal direction and a pair of end edges extending in the transverse direction so as to describe lines intersecting with respective the side edges at an acute angle.

According to further another preferred embodiment of the invention on the first aspect thereof, the queues of compressed spots overlap projecting corners defined by intersections of the side edges and the end edges in the thickness-reduced region.

The present invention on the second aspect thereof relates to an apparatus used to make the disposable bodily fluid handling composite pad by the method according to the present invention on the first aspect thereof.

An improvement in such apparatus according to the present invention on the second aspect thereof has features as follow: at least one of the paired compression rolls is provided on a peripheral surface thereof with embossing dies adapted to compress the continuous web comprising the bodily fluid absorbing layer and the bodily fluid impervious layer both in a form of continuum and permanently attached and thereby to form the continuous web with the thickness-reduced regions; and an individual die of the embossing dies on the one of the paired compression rolls has a dimension on the top thereof as measured in the circumferential direction such that the thickness-reduced regions in one of the first pads and next one in the machine direction of the first pads opposed to one another can be formed as one with the same die.

According to one preferred embodiment of the present invention on the second aspect thereof, the embossing dies are intermittently formed on the one of the paired compression rolls in the circumferential direction as well as in the axial direction thereof.

According to another preferred embodiment of the present invention on the second aspect thereof, the individual one of embossing dies is symmetrical with respect to a center line bisecting the dimension of the individual one as viewed in the axial direction of the one of the paired compression rolls as well as the circumferential direction of the one of the paired compression rolls and contoured by a pair of lateral regions extending in parallel to each other in the circumferential direction and a pair of end regions extending in the axial direction so as to describe lines intersecting with respective the lateral regions at an acute angle.

According to still another preferred embodiment of the present invention on the second aspect thereof, the apparatus further includes a device used to put flat and separably attach the bodily fluid absorbing web to the bodily fluid impervious layer of the worked web to form the first composite web and the device is provided in a form of a heatable second paired compression rolls located downstream of the paired compression rolls used to form the thickness-reduced regions in the worked web.

According to yet another preferred embodiment of the present invention on the second aspect thereof, the paired second compression rolls are adapted to form the body fluid absorbing layer constituting the first composite web with two bilaterally symmetric queues of compressed spots extending in the longitudinal direction so that the bodily fluid impervious layer and the bodily fluid absorbing web may be seperably attached to each other under mechanical entanglements and wherein a first tension controller is provided in any upstream of the paired compression rolls and the second paired compression rolls as viewed in the machine direction to act on any one of the web and the worked web running in the machine direction and a second tension controller is provided on upstream of the second paired compression rolls to act on the bodily fluid absorbing web running in the machine direction.

Effect of the Invention

The method and the apparatus for making the disposable bodily fluid handling composite pad according to the present invention facilitate, in the step of continuously making one component pad constituting each composite pad, the component pad to be formed on longitudinally opposite ends thereof with thickness-reduced regions.

IDENTIFICATION OF REFERENCE NUMERALS USED IN THE DRAWINGS 10 composite pad (composite panty liner)
11 first pad (upper liner)
11a end
11b end
12 second pad (lower liner)
20 compressed spots
21 compressed spots
22 compressed spots
23 thickness-reduced region
24 thickness-reduced region
31 bodily fluid absorbing layer
32 bodily fluid absorbing layer 33 bodily fluid impervious layer
41 bodily fluid absorbing layer
42 bodily fluid absorbing layer
43 bodily fluid absorbing layer
44 bodily fluid impervious layer
61 embossing die
61a top
72a side edge
73a end edge
74a projecting corner
111 web
113 worked web (third laminated web)
115 bodily fluid absorbing web
116 first composite web
117 second composite web
121 continuum (web)
122 continuum (web)
134 first tension controller
135 paired compression rolls
301 second tension controller
302 second paired compression rolls

DETAILED DESCRIPTION OF THE PREFERRED EMBODIMENTS

Details of the present invention will be more fully understood from the following description of a composite panty liner as a typical embodiment of the disposable bodily fluid handling composite pad obtained by the method according to the first aspect of the present invention.

Figure 1:
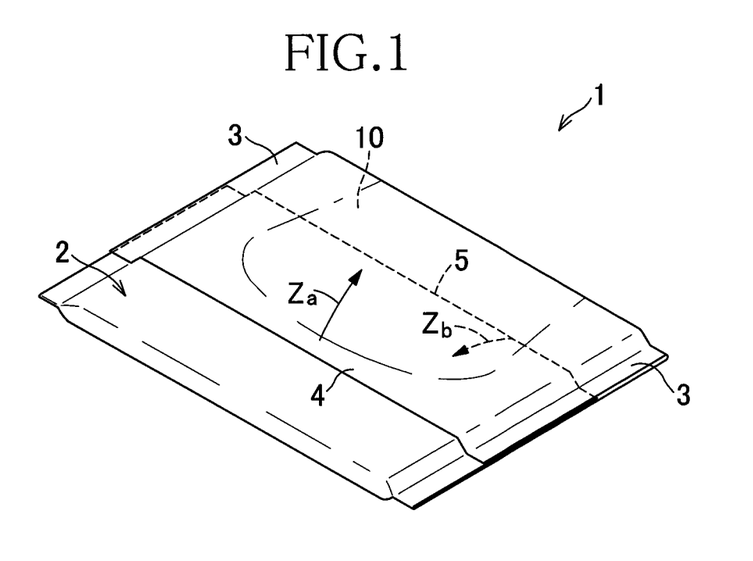
FIG. 1 is a perspective view of an envelope for a composite panty liner.

FIG. 1 is a perspective view of an envelope 1 for the panty liner. The envelope 1 comprises a plastic film 2 wrapping therein a composite panty liner 10 according to the present invention. The film 2 is folded back onto itself and seperably attached to itself along opposite lateral edges 3. To unwrap the envelope 1 and thereby to take out the composite panty liner 10 from the envelope 1, an outer end 4 may be pulled in a direction indicated by an arrow Za and then an inner end 5 may be pulled in a direction indicated by an arrow Zb.

Figure 2:
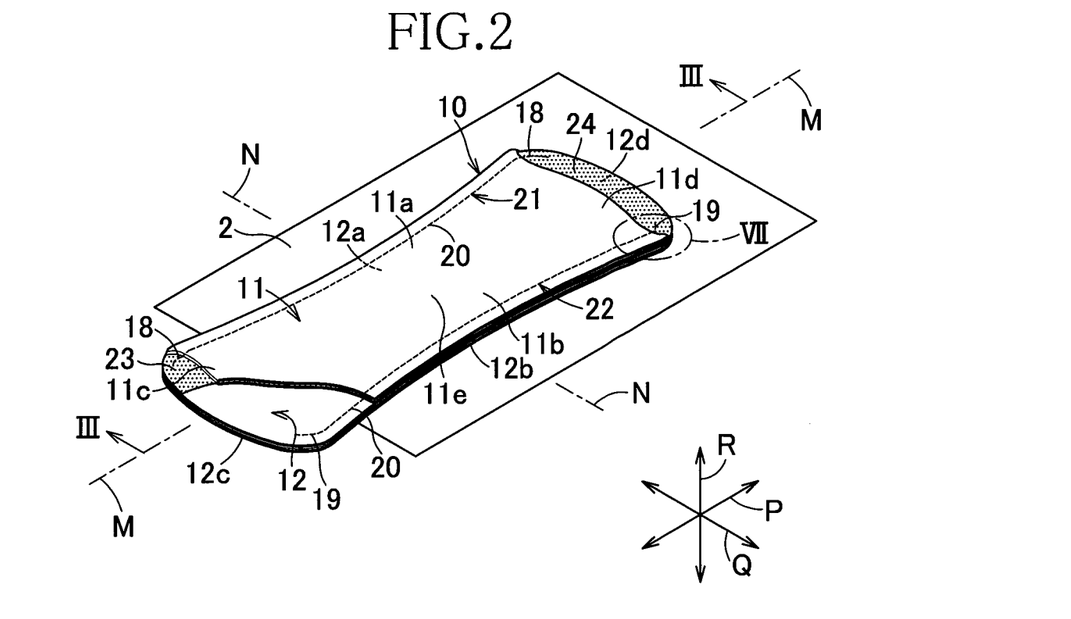
FIG. 2 is a partially cutaway perspective view showing the composite panty liner after unwrapped.
Figure 3:
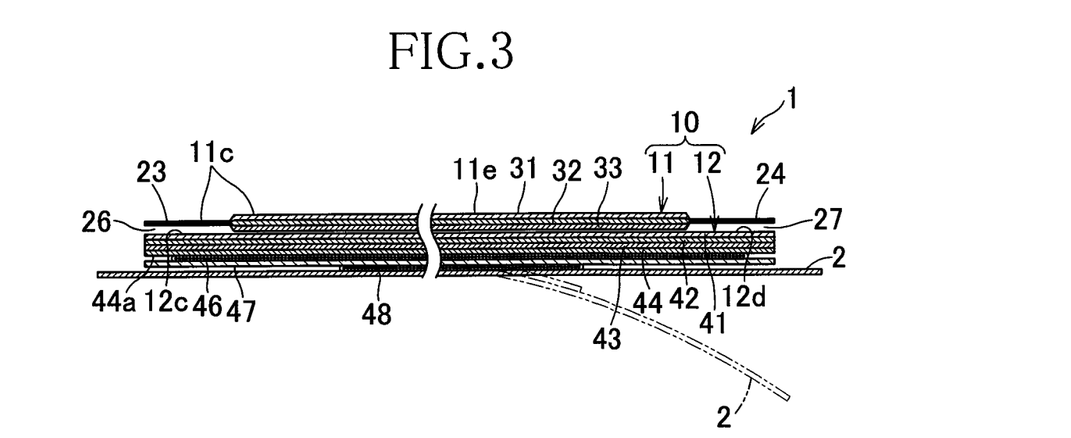
FIG. 3 is a sectional view taken along a line in FIG. 2.

Referring to FIGS. 2 and 3, FIG. 2 is a partially cutaway perspective view showing both the film 2 and the composite panty liner 10 flatly developed after the envelope 1 has been unwrapped from the state as shown by FIG. 1, and FIG. 3 is a sectional view taken along a line in FIG. 2. The composite panty liner 10 comprises an upper liner 11 defining a first pad constituting the bodily fluid handling composite pad according to the invention and a lower liner 12 defining a second pad constituting the bodily fluid handling composite pad according to the invention wherein these two individual liners 11, 12 are put flat and seperably attached together. In this exemplary embodiment, these upper and lower liners 11, 12 are same in shape as well as in size, each having a longitudinal direction P, a transverse direction Q and a thickness direction R, which are orthogonal one to another. Each of the upper liner 11 and the lower liner 12 is shaped so as to be symmetric with respect to the center line M bisecting a dimension in the transverse direction Q as well as the center line N bisecting a dimension in the longitudinal direction P wherein the line corresponds to the center line M. The upper liner 11 and the lower liner 12 are relatively long in the longitudinal direction P and respectively have opposite sides 11a, 11b; 12a, 12b extending in parallel one to another in the longitudinal direction P and opposite ends 11c, 11d; 12c, 12d extending in parallel one to another in the transverse direction Q. The ends 11c, 11d are contiguous to the sides 11a, 11b and the ends 12c, 12d are contiguous to the sides 12a, 12b.

The upper liner 11 and the lower liner 12 are seperably attached together along a first compressed zone 21 formed in the sides 11a, 12a and a second compressed zone 22 formed in the sides 11b, 12b so as to be symmetrical to the first compressed zone 21 in the transverse direction Q. These first and second compressed zones 21, 22 respectively comprise a plurality of small compressed spots 20 intermittently arranged in the longitudinal direction P (See FIG. 7) so as to define respective arrays extending to respectively opposite end portions 18, 18; 19, 19 in the longitudinal direction P, i.e., to the ends 11c, 11d of the upper liner 11 and the ends 12c, 12d of the lower liner 12. As will be described later in detail, the individual small compressed spots 20 are formed by locally compressing, with or without heating, the upper liner 11 and the lower liner 12 put flat together between paired upper and lower compression rolls. In these small compressed spots 20, fibers in the upper liner 11 are forced to be mechanically entangled with fibers in the lower liner 12.

The upper liner 11 comprises a bodily fluid pervious first top sheet 31 formed by non-woven fabric containing thermoplastic synthetic fiber or perforated plastic film, a bodily fluid absorbing first intermediate sheet 32 formed with non-woven fabric containing thermoplastic synthetic fiber and bodily fluid impervious first bottom sheet 33 formed with plastic film or non-woven fabric containing thermoplastic synthetic fiber. These sheets 31, 32, 33 are stacked one upon another and permanently bonded together by hot melt adhesive (not shown) so that the first top sheet 31 and the first intermediate sheet 32 define a bodily fluid absorbing layer while the first bottom sheet 33 defines a bodily fluid impervious layer. The bodily fluid absorbing layer serves to absorb and to retain bodily fluids and the thermoplastic synthetic fiber contained in this layer preferably has been modified to become hydrophilic. This layer may additionally contain liquid-absorbent fiber such as pulp fiber or rayon fiber. The bodily fluid impervious layer serves to prevent bodily fluids absorbed and retained by the bodily fluid absorbing layer from moving downward into the lower liner 12. Such upper liner 11 is formed along the ends 11c, 11d with a third compressed zone 23 and a fourth compressed zone 24, respectively. These third and fourth compressed zones 23, 24 are formed by locally compressing the upper liner 11 at a temperature facilitating hot melt adhesive and/or thermoplastic synthetic fiber contained therein to be easily deformed so that these third and fourth compressed zones 23, 24 may become thinner than an intermediate region 11e extending between the opposite ends 11c, 11d and, in addition, preferably may have a hardness higher than that of the intermediate region 11e (See FIG. 3).

The lower liner 12 comprises a bodily fluid-pervious second top sheet 41 formed by non-woven fabric containing thermoplastic synthetic fiber or perforated plastic film, bodily fluid absorbing second and third intermediate sheets 42, formed by non-woven fabric containing thermoplastic synthetic fiber and a second bottom sheet 44 formed by non-woven fabric containing thermoplastic synthetic fiber. These sheets 41, 42, 43, 44 are stacked one upon another and permanently bonded together by hot melt adhesive (not shown) so that the second top sheet 41 and the second and third intermediate sheet 42, 43 cooperate together to define a layer serving to absorb and to retain bodily fluids while the second bottom sheet 44 defines a bodily fluid impervious layer serving to prevent bodily fluids from moving downward to the wearer's garment. The thermoplastic synthetic fiber contained in the layer serving to absorb and to retain preferably has been previously modified to become hydrophilic. This layer may additionally contain liquid-absorbent fiber such as pulp fiber. The second bottom sheet 44 has a garment-contact surface 44a adapted to come in contact with the wearer's garment (not shown) and the garment-contact surface 44a is coated with pressure-sensitive adhesive 46. The pressure-sensitive adhesive 46 is protectively covered by a separator 47 which is, in turn, permanently bonded to the film 2 by adhesive 48.

To wear such composite panty liner 10, the separator 47 is peeled off from the lower liner 12 to expose the pressure-sensitive adhesive 46 coated on the lower liner 12 and this pressure-sensitive adhesive 46 is utilized to fix the composite panty liner 10 to the wearer's garment. When the upper liner 11 is soiled, the third compressed zone 23 or the fourth compressed zone 24 of the upper liner 11 may be nipped by fingers and the upper liner 11 may be peeled off from the lower liner 12 to use the lower liner 12 as substitute for the soiled upper liner 11. It is easy to distinguish the third compressed zone 23 or the fourth compressed zone 24 with respect to the lower liner 12 and to nip by the fingers because these third and fourth compressed zones 23, 24 of the upper liner 11 still stacked on the lower liner 12 are formed to be sufficiently thinner than the remaining zone of the upper liner 11 to assure gaps 26, 27 (See FIG. 3) between the compressed zones 23, 24 and the lower liner 12. If the compressed zones 23, 24 are intentionally formed by locally compressing the upper liner 11 to provide these compressed zones 23, 24 with hardness and bending stiffness higher than those of the remaining zones, the compressed zones 23, 24 can be more easily nipped. The composite panty liner 10 is symmetric with respect to the center line M as well as the center line N so far as this specific embodiment is concerned, and, therefore, it can be put on the wearer's body with either the third compressed zone 23 or the fourth compressed zone 24 in front. However, it is not essential for the composite panty liner 10 to be symmetrical with respect to the center line N and the composite panty liner 10 may be shaped to be asymmetrical about the center line N depending on its intended purpose without departing from the scope of the invention. It is also not essential for the composite panty liner 10 that the upper liner 11 and the lower liner 12 should be same in shape as well as in size, and an alternative embodiment such that the lower liner 12 is larger than the upper liner 11 is within the technical scope of the present invention.

Figure 4:
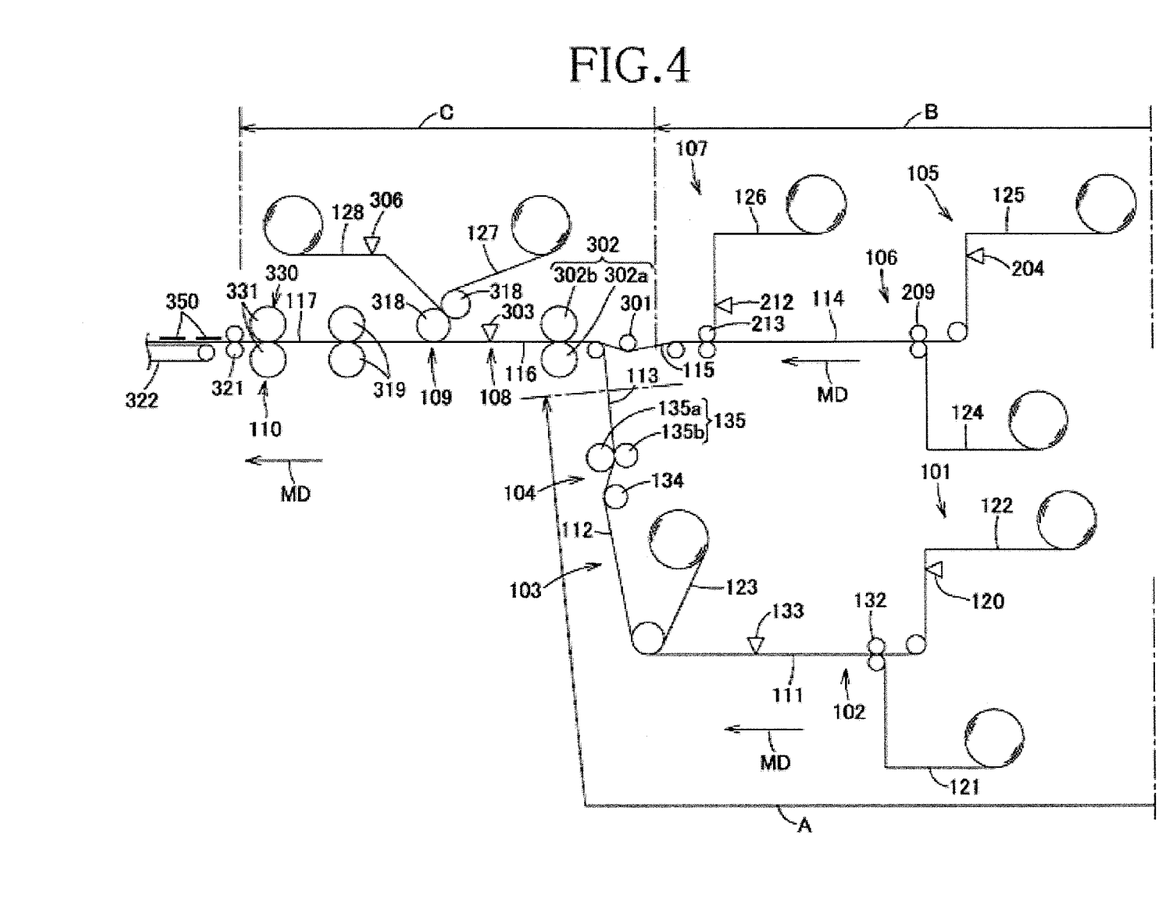
FIG. 4 is a schematic diagram illustrating a process of making the composite panty liner.

FIG. 4 is a schematic diagram exemplarily illustrating a process of making the composite panty liner 10. The process comprises a first section A for making the upper liner 11, a second section B substantially for making the lower liner 12 and a third section C provided downstream of the first and second sections A, B to obtain the finished composite panty liner 10.

The first section A includes a first step 101 through a fourth step 104. Specifically, in the first step 101, a first web 121 from which the first top sheet 31 will be obtained and a second web 122 from which the first intermediate sheet 32 will be obtained are fed from the right hand as viewed in FIG. 4 in a machine direction MD. Also in the step 101, a coater 120 is used to coat one surface of the second web 122 with hot melt adhesive (not shown).

In the second step 102, the first and second webs 121, 122 are fed to nip rolls 132 rotating to feed these webs in the machine direction MD and thereby these webs 121, 122 are bonded together by hot melt adhesive coated on the second web 122 to obtain a first laminated web 111. The second web 122 constituting this first laminated web 111 is coated with hot melt adhesive (not shown) using a coater 133.

In the third step 103, a third web 123 from which the first bottom sheet 33 will be obtained is fed in the machine direction MD and bonded to the first laminated web 111 by hot melt adhesive coated on the first laminated web 111 using the coater 133 to obtain a second laminated web 112.

In the fourth step 104, the second laminated web 112 being kept by a first tension controller 134 under a constant tension in the machine direction MD is fed to first paired compression rolls 135 consisting of a first roll 135a and a second roll 135b. Passing through the first paired compression rolls 135, the second laminated web 112 are locally compressed, more specifically, respective zones thereof along which the third and fourth compressed zones 23, 24 will be formed are compressed to obtain a third laminated web 113 partially thickness-reduced.

The second section B includes a fifth step 105 through a seventh step 107. Specifically, in the fifth step 105, a fourth web 124 from which the second top sheet 41 will be obtained and a fifth web 125 from which the second intermediate sheet 42 will be obtained are fed from the right hand as viewed in FIG. 4 in a machine direction MD. Also in the step 105, a coater 204 is used to coat one surface of the fifth web 125 with hot melt adhesive (not shown).

In the sixth step 106, fourth and fifth webs 124, 125 are fed to nip rolls 209 and bonded to each other by hot melt adhesive coated on the fifth web 125 to obtain a fourth laminated web 114.

In the seventh step 107, a sixth web 126 from which the third intermediate sheet 43 will be obtained is fed in the machine direction MD and, in the course of feeding this sixth web 126, a coater 212 is used to coat one surface of the sixth web 126 with hot melt adhesive (not shown). Also in the seventh step 107, nip rolls 213 rotating in the machine direction MD are used to bond the fourth laminated web 114 to the sixth web 126 coated with hot melt adhesive and thereby to obtain a fifth laminated web 115.

The third section C includes an eighth step 108 through a tenth step 110. Specifically, in the eighth step 108, the fifth laminated web 115 being kept by a second tension controller 301 under a desired tension in the machine direction MD is put flat together with the third laminated web 113 coming from the first section A and fed to second paired compression rolls 302 consisting of a roll 302a and a roll 302b. The roll 302a is provided on its peripheral surface with embossing dies (not shown) corresponding to the respective small compressed spots 20 (See FIGS. 2 and 7) while the roll 302b has a smooth peripheral surface including portions facing the embossing dies of the roll 302a. Passing through the second paired compression rolls 302, the third laminated web 113 and the fifth laminated web 115 are locally compressed, more specifically, respective zones thereof along which the first compressed zone 21 and the second compressed zones 22 will be formed, respectively, are compressed so that at least the third web 123 of the third laminated web 113 and at least the fourth web 124 of the fifth laminated web 115 may be mechanically entangled together. In this way, a first composite web 116 is obtained, in which the laminated web 113 and the laminated web 115 are seperably attached. To enhance a compressing effect, it is also possible to use the second paired compression rolls 302 under heating. Also in the eighth step 108, a coater 303 is used to coat the sixth web 126 constituting the first composite web 116 with hot melt adhesive (not shown).

In the ninth step 109 of the third section C, a seventh web 127 from which the second bottom sheet 44 of the composite panty liner 10 will be obtained and an eighth web 128 from which the separator 47 of the composite panty liner 10 will be obtained are fed in the machine direction MD. A coater 306 is used to coat one surface of the eighth web 128 with hot melt adhesive (not shown). The seventh web 127 and the eighth web 128 are fed to paired nip rolls 318 to bond these seventh and eighth webs 127, 128 to each other by adhesive previously coated on the eighth web 128. Then the seventh web 127 is put flat upon the sixth web 126 constituting the first composite web 116 previously coated with adhesive. The seventh web 127, the eighth web 128 and the first composite web 116 are fed so as to pass through paired nip rolls 319 and to be bonded together. In this way, second composite web 117 is obtained.

In the tenth step 110 of the third section C, the second composite web 117 is continuously fed to a cutter 330 comprising paired rolls 331 rotating in the machine direction MD and thereby individual composites 350 each consisting of the upper liner 11, the lower liner 12 and the separator 47 are successively cut out from the second composite web 117.

In the downstream steps subsequent to the tenth step 110, appropriate means such as paired conveyer rolls 321 or an endless belt 322 is used to convey the individual composites 350 in the machine direction MD and, in the course of conveying, these composites 350 are successively wrapped by the plastic film 2 to obtain the envelopes 1 each containing therein the composite panty liner 10 (See FIG. 1). The composite 350 corresponds to the composite panty liner 10 shown by FIG. 2.

Figure 5:
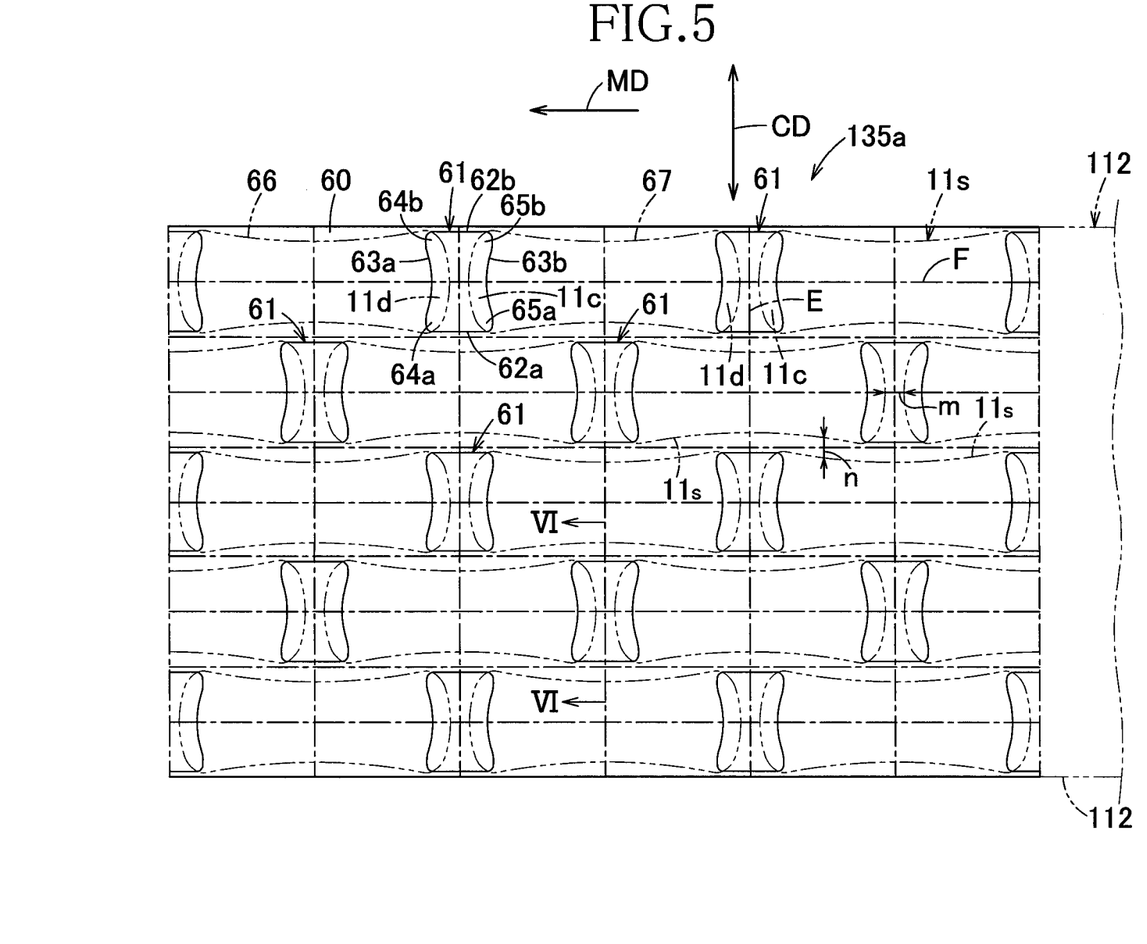
FIG. 5 is a diagram showing a peripheral surface of a first compression roll as flatly developed.
Figure 6:
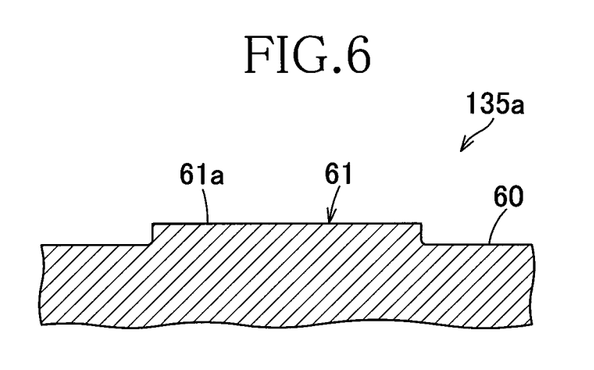
FIG. 6 is a sectional view taken along a line VI-VI in FIG. 5.

FIGS. 5 and 6 illustrate the first paired compression rolls 135 used in the first section A of the process schematically illustrated by FIG. 4. The first paired compression rolls 135 consist of the first roll 135a rotating so as to feed the second laminated web 112 in the machine direction MD and the second roll 135b (See FIG. 4) wherein the first roll 135a is formed on its peripheral surface 60 with a plurality of the embossing dies 61 (See FIG. 6) and the second roll 135b has the smooth peripheral surface. FIG. 5 illustrates the peripheral surface 60 of the first roll 135a flatly developed in the machine direction MD and FIG. 6 is a sectional view taken along a line VI-VI in FIG. 5, schematically illustrating a top 61a of the embossing die 61. Referring to FIG. 5, the second laminated web 112 fed to the first paired compression rolls 135 and a contour of each region 11s of the second laminated web 112 corresponding to the upper liner 11 are indicated by imaginary lines. The individual regions 11s make a plurality of queues each extending in the machine direction MD and these queues are adjacent one another in the cross direction CD. It should be noted that, between each pair of the regions 11s, 11s being adjacent in the cross direction CD there is an offset in the machine direction MD approximately by a half-length of the region 11s. The paired regions 11s being adjacent in the machine direction MD are spaced from each other by a dimension m and the paired regions 11s in the cross direction CD are spaced from each other by a dimension n.

Referring again to FIG. 5, the peripheral surface 60 of the first roll 135a is formed intermittently in the machine direction MD as well as in the cross direction CD with the embossing dies 61 wherein each of the embossing dies 61 is symmetric in the machine direction MD as well as in the cross direction CD. In other words, the embossing die 61 is symmetrically formed with respect to a center line E extending in the cross direction CD so as to bisect a dimension of the embossing die 61 in the machine direction MD and symmetric also with respect to another center line F extending in the machine direction MD so as to bisect a dimension of the embossing die 61 in the cross direction CD. Each of the embossing dies 61 is defined by a pair of opposite lateral regions 62a, 62b extending in parallel to each other in the machine direction MD and a pair of opposite end regions 63a, 63b extending in the cross direction CD so as to describe curves respectively. The opposite ends of the lateral regions 62a, 62b are connected to the end regions 63a, 63b, respectively. The respective lateral regions 62a, 62b intersect with the end region 63a at an acute angle to define projecting corners 64a, 64b extending forward in the machine direction MD. In the similar manner, the respective lateral regions 62a, 62b intersect with the end region 63b to define projecting corners 65a, 65b extending rearward in the machine direction MD.

With respect to each pair of the regions 11s of the embossing die 61 corresponding to the upper liners 11 moving in tandem in the machine direction MD as the first roll 135a rotates to feed the second laminated web 112 in the machine direction MD, it is assumed that the front one is referred to as a predetermined region 66 and the rear one is referred to as a predetermined region 67. The embossing die 61 of the first roll 135a operates over a full dimension (length) thereof to compress the end 11d (See FIGS. 2 and 3) of the region 66 and then to compress the end 11c of the region 67. In other words, these ends 11d, 11c can be compressed by a single die 61. It should be appreciated that these ends 11d, 11c successively compressed by one and same embossing die 61 are included in the respective regions 66, 67 being adjacent and opposed to each other in the machine direction MD.

The step of compressing the second laminated web 112 between the first roll 135a formed with the die 61 as have been described above and the second roll 135b begins at the moment when the projecting corners 64a, 64b come in contact with the second laminated web 112 and ends at the moment when the projecting corners 65a, 65b leave the second laminated web 112. In other words, the projecting corners 64a, 64b of the embossing die 61 come in contact first with the second laminated web 112 and then the projecting corners 65a, 65b come in contact with the second laminated web 112. It should be appreciated that the second laminated web 112 fed to the first paired compression rolls 135 may be regulated by the first tension controller 134 immediately before the web 112 passes through the first paired compression rolls 135 so as to be kept under a desired tension in the machine direction MD to prevent the first, second and third webs 121, 122, 123 constituting the second laminated web 112 from getting wrinkled or sagging in the course of being compressed by the first paired compression rolls 135.

The first roll 135a constituting the first paired compression rolls 135 is provided on its peripheral surface with a plurality of the embossing die 61 in a pattern as illustrated by FIG. 5. Specifically, there is an offset between the individual embossing die 61 in one queue extending in the machine direction MD and the individual embossing die 61 in the other queue adjacent in the cross direction CD. With such layout, the embossing dies 61 successively act upon the second laminated web as the first paired compression rolls rotate. As a consequence, compressive force desired to form a plurality of the third and fourth compressed zones 23, 24 on the second laminated web 112 over its full width may be reduced in comparison to a layout without offset between the individual embossing die in each pair of the queues adjacent in the cross direction CD. Construction of the first paired compression rolls 135 can be correspondingly simplified and manufacturing of the paired compression rolls 135 also can be correspondingly facilitated.

In the eighth step 108 of the third section C, the second tension controller 301 acts on the fifth laminated web 115 immediately before the latter passes through the second paired compression rolls 302 to keep the fifth laminated web 115 under a desired tension in the machine direction MD and thereby prevents the fifth laminated web 115 from getting wrinkled or sagging in the course of passing through the second paired compression rolls 302. The third laminated web 113 to be combined with the fifth laminated web 115 in the eighth step 108 has already been subjected to the first tension controller 134 in the fourth step 104 and remains under a given tension in the machine direction MD in the course of passing through the second paired compression rolls 302. However, if it is desired to keep the third laminated web 113 also under a tension comparable with the tension of the fifth laminated web 115, the third laminated web 113 also may be subjected to the second tension controller 301 immediately before the web 113 passes through the second paired compression rolls 302. By controlling both the third laminated web 113 and the fifth laminated web 115 to be kept under the same tension and thereby to prevent them from getting wrinkled or sagging, one of these two laminated webs 113, 115 does not sag at the compression by the second paired rolls 302. Consequentially, both the upper liner 11 and the lower liner 12 are flat in the composite 350 cut out from the second composite web 117 in the tenth step 110 and the composite 350 is free from undesirable rolling back.

The composite 350 free from undesirable rolling back obtained in the manner as has been described above is advantageous for conveyance thereof in the machine direction MD following the tenth step 110 whether such conveyance is carried out by the paired nip rolls 321 or by the endless conveyor belt 322. Specifically, the composite 350 free from undesirable rolling up can smoothly pass through the paired nip rolls 321 in the former case and the composite 350 can be well stabilized on the endless belt 322 in the latter case. Particularly when the composite 350 is transported by the endless conveyor belt 322 under vacuum, stability of the composite 350 on the endless conveyor belt 322 is improved in proportion to the flatness of the composite 350. In addition, assumed that the upper liner 11 in the composite 350 has been formed with the third compressed zone 23 or the fourth compressed zone 24 and at least the front end of the composite 350 has been compressed to be thinner and preferably harder than the remaining region, passing of the composite 350 through the paired nip rolls 321 at a high velocity is achieved without curling or rolling up the end 11c or the end 11d of the upper liner 11 from the lower liner 12 at a moment of passing through the paired nip rolls 321 or in the course of being conveyed. At least the front end of the composite 350 may be formed with the compressed zone to facilitate the composite 350 to be smoothly fed into the paired nip rolls 321.

Figure 7:
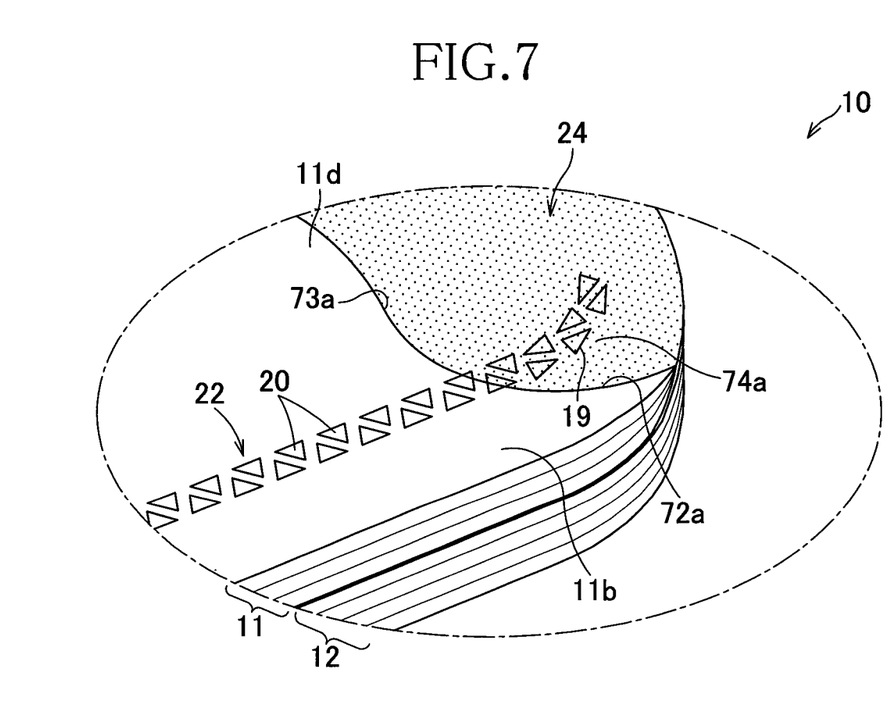
FIG. 7 is a scale-enlarged view of a region VII in FIG. 2.

FIG. 7 illustrates a region VII of the composite panty liner 10 in FIG. 2 in an enlarged scale. The region VII includes only a part of the end 11d of the upper liner 11 and, in this end 11d, the second queue 22 of the small compressed spots 20 overlaps the fourth compressed zone 24. The fourth compressed zone 24 in FIG. 7 is defined in the vicinity of the lateral region 62a and the end region 63a of the embossing die 61 in FIG. 5 and includes a side edge 72a corresponding to the rectilinear lateral region 62a, an end edge 73a corresponding to the arcuate end region 63a and a projecting corner 74a corresponding to the acute projecting corner 64a defined by intersection of the lateral region 62a and the end region 63a. At the projecting corner 74a, the fourth compressed zone 24 and the second compressed zone 22 overlap each other. It will be apparent from the process schematically illustrated by FIG. 4, the upper liner 11 is formed by the first paired compression rolls 135 with the fourth compressed zone 24 and then formed by the second paired compression rolls 302 with the second compressed zone 22. As will be apparent from the layout of the embossing dies exemplarily illustrated by FIG. 5, the projecting corners 64a, 64b of the embossing die 61 come first in contact with the second laminated web 112 to form the projecting corner 74a of the fourth compressed zone 24. Then, the arcuate end edge 63a of the embossing die 61 extending between the projecting corners 64a, 64b come in contact with the second laminated web 112 to form the end 73a in the fourth compressed zone 24.

By compressing the second laminated web 112 in this order using the embossing die 61 including such projecting corners 64a, 64b, it is assured that these projecting corners 64a, 64b can compress the second laminated web 112 to form the projecting corner 74a without being affected by any differential thickness even when the thickness of the second laminated web 112 in the cross direction CD is thicker in the region defined between the projecting corners 64a, 64b than in the region coming in contact with the projecting corners 64a, 64b. Thereafter the second paired compression rolls 302 is used to compress the third laminated web 113 against the fifth laminated web 115 and thereby the second compressed zone 22 is formed so as to overlap the projecting corner 74a which has reliably been compressed to a high density. As a consequence, it is assured that compressed fiber or film in the projecting corner 74a partially cuts into the fifth laminated web 115 and thereby the third laminated web 113 and the fifth laminated web 115 are brought into mechanical entanglements in the projecting corner 74a. While the first compressed zone 21 and the second compressed zone 22 in the first composite web 116 formed by the second paired compression rolls 302 should serve to attach the upper liner 11 to the lower liner 12 in a separable fashion, the upper liner 11 and the lower liner 12 might begin to be peeled off from each other at one of the opposite ends 18, 18 and/or 19, 19 (See FIG. 2) of the first compressed zone 21 and/or the second compressed zone 22, respectively. However, the opposite ends 18, 18; 19, 19 of the first and second compressed zones 21, 22, respectively, may be formed so as to overlap the projecting corners of the upper liner 11 formed by the associated projecting corners 64a, 64b, 65a, 65b of the embossing die 61, just as in the exemplary embodiment illustrated by FIG. 7 wherein the end 19 of the second compressed zone 22 is placed upon the projecting corner 74a of the fourth compressed zone 24, to eliminate a potential problem that the upper liner 11 and the lower liner 12 might unintentionally begin to be peeled apart from each other at one of the opposite ends 18, 18; 19, 19 of the first compressed zone 21 and the second compressed zone 22, respectively.

Without departing from the scope of the invention, it is possible to make the first composite web 116 by cutting out the upper liner 11 exemplarily illustrated by FIG. 2 from the third laminated web 11 obtained by the first paired compression rolls 135, then to place the upper liner 11 upon the fifth laminated web 115 and to compress this assembly by the second paired compression rolls 302. In the upper liner 11 formed in this manner, the upper liner 11 runs with the end edge 11c as its front end in the machine direction MD and this end edge 11c has the compressed zone. Consequentially, the upper liner can smoothly go into the paired nip rolls (not shown).

The second and third intermediate sheets 42, 43 of the lower liner 12 used in the illustrated embodiment serve to bring the bodily fluid absorbing capacity to a desired level and at the same time to provide the lower liner 12 with stiffness sufficient to prevent the lower liner 12 from becoming unacceptably flexible after the upper liner 11 has been peeled off. In view of this, if a single intermediate sheet can assure to provide the lower liner 12 with both an appropriate bodily fluid absorbing capacity and an appropriate stiffness, the present invention can be reduced to practice without another intermediate sheet.

The invention claimed is:

1. A method of making a disposable bodily fluid handling composite pad having a longitudinal direction, a transverse direction and a thickness direction being orthogonal one to another, and said pad comprising a first bodily fluid absorbing pad and a second bodily fluid absorbing pad, said first bodily fluid absorbing pad comprising a bodily fluid absorbing layer and a bodily fluid impervious layer attached permanently together in said thickness direction, at least one of opposite ends of the first bodily fluid absorbing pad as viewed in said longitudinal direction is formed so as to be thinner than an intermediate region defined between said opposite ends, and said second bodily fluid absorbing pad being seperably attached to said bodily fluid impervious layer of said first bodily fluid absorbing pad, wherein said method comprises the steps of:

feeding a continuous web, which includes said bodily fluid absorbing layer and said bodily fluid impervious layer permanently attached to each other, in a machine direction, through paired compression rolls rotating in said machine direction;

compressing regions of said continuous web, which correspond respectively to said at least one of said opposite ends, by said paired compression rolls to reduce the thickness of said regions of the continuous web to obtain a worked web along which thickness-reduced regions corresponding to said opposite ends are arranged at predetermined intervals in said machine direction;

non-adhesively attaching a bodily fluid absorbing web to (i) said bodily fluid impervious layer of the worked web while feeding said worked web or to (ii) a plurality of said first bodily fluid absorbing pads cut out from said worked web in said machine direction, to obtain a first composite web defining the first bodily fluid absorbing pad;

permanently and directly attaching a bodily fluid impervious web to said bodily fluid absorbing web constituting said first composite web so that said bodily fluid absorbing web directly contacts the bodily fluid impervious web;

coating said bodily fluid impervious web with pressure-sensitive adhesive;

covering said pressure-sensitive adhesive with a web to obtain a second composite web defining the second bodily fluid absorbing pad, wherein the bodily fluid impervious web of the second composite web is separably attachable to a garment of a wearer by said pressure-sensitive adhesive when the web is removed; and cutting said second composite web to obtain said composite pad.

2. The method according to claim 1, wherein said worked web is formed with two or more queues of said thickness-reduced regions that correspond to the first bodily fluid absorbing pads and are arranged in a cross direction orthogonal to said machine direction.

3. The method according to claim 2, wherein in each pair of said adjacent queues of said thickness-reduced regions arranged in the cross direction, said thickness-reduced regions are individually offset so as not to be adjacent one another as viewed in the cross direction of said continuous web.

4. The method according to claim 1, wherein
said step of non-adhesively attaching said bodily fluid absorbing web to said bodily fluid impervious layer comprises locally compressing, said worked web or a plurality of said first bodily fluid absorbing pads cut out from the worked web, with said bodily fluid absorbing web to form queues of compressed spots at which said worked web or said plurality of first bodily fluid absorbing pads is brought into mechanical entanglement with said bodily fluid absorbing web, and
said compressed spots partially overlap said thickness-reduced regions.

5. The method according to claim 1, wherein each of said thickness-reduced regions is contoured, on said bodily fluid absorbing layer, by a pair of side edges extending in parallel to each other in said machine direction and a pair of end edges extending in said cross direction and the end edges intersect with respective said side edges at an acute angle.

6. The method according to claim 5, wherein
said step of non-adhesively attaching said bodily fluid absorbing web to said bodily fluid impervious layer comprises locally compressing said worked web where a plurality of said first bodily fluid absorbing pads is formed with said bodily fluid absorbing web to form queues of compressed spots at which said worked web or said plurality of first bodily fluid absorbing pads is brought into mechanical entanglement with said bodily fluid absorbing web, and
said queues of compressed spots overlap projecting corners defined by intersections of said side edges and said end edges in said thickness-reduced regions.

7. The method according to claim 1, wherein the thickness-reduced regions that correspond to the opposite ends of the first bodily fluid absorbing pad and are compressed at the step of compressing, and
the thickness reduced regions are spaced from each other in the machine direction and spaced from each other in the cross direction.

8. The method according to claim 1, wherein said step of non-adhesively attaching said bodily fluid absorbing web to said bodily fluid impervious layer comprises compressing the worked web and the bodily fluid absorbing web so as to mechanically entangle the bodily fluid impervious layer of the worked web and the bodily fluid absorbing web together.

9. The method according to claim 8, wherein said worked web is formed with two or more queues of said thickness-reduced regions that correspond to the first bodily fluid absorbing pads and are arranged in a cross direction orthogonal to said machine direction.

10. The method according to claim 9, wherein each of said thickness-reduced regions is contoured, on said bodily fluid absorbing layer, by a pair of side edges extending in parallel to each other in said machine direction and a pair of end edges extending in said cross direction and the end edges intersect with respective said side edges at an acute angle.

11. The method according to claim 10, wherein the thickness-reduced regions that correspond to the opposite ends of the first bodily fluid absorbing pad and are compressed at the step of compressing, and
the thickness reduced regions are spaced from each other in the machine direction and spaced from each other in the cross direction.

12. The method according to claim 8, wherein said compressing the worked web and the bodily fluid absorbing web is performed to obtain queues of compressed spots which extend in the machine direction and partially overlap said thickness-reduced regions.

* * * * *